United States Patent [19]
Cowley et al.

[11] Patent Number: 5,751,214
[45] Date of Patent: May 12, 1998

[54] PATIENT ACTIVITY MONITORING DEVICE WITH MULTIPLE SENSORS

[75] Inventors: Tom J. Cowley, Tiburon; Larry O. Bower, Santa Rosa; Philip S. Egan, Fairfax, all of Calif.

[73] Assignee: AlertCare, Inc., Mill Valley, Calif.

[21] Appl. No.: 571,462

[22] Filed: Dec. 13, 1995

[51] Int. Cl.⁶ ............................................. G08B 23/00
[52] U.S. Cl. ....................... 340/573; 340/568; 340/548; 340/687; 340/689; 340/693; 128/886; 128/710
[58] Field of Search ............................ 340/573, 568, 340/686, 687, 689, 693, 548; 128/886, 710

[56] References Cited

U.S. PATENT DOCUMENTS

| | | | |
|---|---|---|---|
| 4,216,462 | 8/1980 | McGrath et al. | 128/710 |
| 4,263,586 | 4/1981 | Nicholas | 340/568 |
| 4,536,755 | 8/1985 | Holzgang et al. | 340/573 |
| 4,577,185 | 3/1986 | Andersen | 340/573 |
| 4,750,197 | 6/1988 | Denekamp et al. | 340/825.35 |
| 4,838,275 | 6/1989 | Lee | 128/670 |
| 4,938,476 | 7/1990 | Brunelle et al. | 272/93 |
| 4,947,152 | 8/1990 | Hodges | 340/573 |
| 4,958,145 | 9/1990 | Morris | 340/689 |
| 4,972,177 | 11/1990 | Nolan | 340/573 |
| 5,008,654 | 4/1991 | Callaway | 340/686 |
| 5,038,137 | 8/1991 | Lloyd | 340/573 |
| 5,047,750 | 9/1991 | Hector | 340/573 |
| 5,137,033 | 8/1992 | Norton | 128/886 |
| 5,146,206 | 9/1992 | Callaway | 340/375 |
| 5,283,549 | 2/1994 | Mehaffey et al. | 340/521 |
| 5,398,019 | 3/1995 | Barnett et al. | 340/689 |
| 5,410,297 | 4/1995 | Joseph et al. | 340/573 |
| 5,473,310 | 12/1995 | Ko | 340/309.15 |
| 5,494,046 | 2/1996 | Cross | 128/782 |
| 5,600,108 | 2/1997 | Newham | 340/573 |
| 5,600,305 | 2/1997 | Stafford et al. | 340/573 |
| 5,633,627 | 5/1997 | Newham | 340/573 |

FOREIGN PATENT DOCUMENTS

| | | |
|---|---|---|
| 2186723 | 8/1987 | United Kingdom . |
| 2276969 | 12/1994 | United Kingdom . |
| WO88/02237 | 4/1988 | WIPO . |
| WO91/08704 | 6/1991 | WIPO . |

OTHER PUBLICATIONS

RF Technologies, Inc. brochure (2 pp.), "Code Alert CA900" (Bed and Chair Alarm), published before Dec. 13, 1995.

Wander Guard, Inc. advertisement (1 p.), "Reduce the Risk of Falls!", published before Dec. 13, 1995.

Wander Guard, Inc. brochure (2 pp.), "Catch–All Door Security System", published before Dec. 13, 1995.

*Primary Examiner*—Jeffery Hofsass
*Assistant Examiner*—Benjamin C. Lee
*Attorney, Agent, or Firm*—Klarquist Sparkman Campbell Leigh & Whinston, LLP

[57] ABSTRACT

A portable multi-purpose device for monitoring patient movement in a number of different ways. The device includes a data processor programmed to respond to signals from multiple different external sensors that easily connect to the device through a jack in the device housing. If patient movement beyond a limit is sensed, the device generates an alarm for an attendant. To sense the different types of patient movement, one sensor is simply substituted for another. Examples of sensors include tether, door monitoring, and weight sensors. The device protects against unauthorized disabling of the sensors by sounding an alarm if a sensor is unplugged from the device impermissibly. The device provides power to sensors that require power to operate, reducing the need for additional power sources. The device also stores patient data (e.g., number of alarms, time before attendance response, etc.) during a given time period for evaluating a patient's care.

11 Claims, 6 Drawing Sheets

PATIENT ACTIVITY MONITORING DEVICE WITH MULTIPLE SENSORS

FIELD OF THE INVENTION

This invention relates generally to apparatus and method for monitoring patient activity. More particularly, this invention relates to an apparatus and method for notifying an attendant of a patient's movement beyond an area of confinement, such as from a bed or a room.

BACKGROUND OF THE INVENTION

Patient activity monitoring devices of limited capability have been in use for some time. A prime example of such a device is shown and described in U.S. Pat. No. 4,536,755, assigned to the present assignee and incorporated by reference herein. The device mounts to the leg of a patient and detects through movement of mercury within an internal switch whether the patient has arisen to an ambulatory position from a reclined position, generating an alarm if he has done so. Other devices of various pneumatic, fluid, mechanical and magnetic designs are also known for sensing a patient's weight in a bed and generating an alarm if the patient leaves the bed.

The primary drawback of these prior devices is their limited use. To monitor a patient's position in a bed, one device is needed. To monitor a patient's presence in the bed, another device is required. And to monitor a patient's presence in a room, still another device is required. The cost to monitor all such movements by procuring multiple devices can be considerable.

Another drawback is the limited information these devices provide to attending personnel—they simply notify an attendant by an alarm that the patient has impermissibly moved. No information is provided regarding how often and when the patient moved, the length of time before an attendant responded to an alarm, or other details that can be used to improve care for the patient.

An objective of the invention, therefore, is to provide an apparatus and method for monitoring patient activity that can detect a number of different patient movements through the use of different sensors connectable to a single device.

Another objective of the invention is to provide an apparatus and method for monitoring patient activity that collects useful information on the nature of the patient's movement and attendant's responses during a given time period.

SUMMARY OF THE INVENTION

Apparatus in accordance with the invention monitors a patient's condition, such as movement beyond a prescribed limit. The apparatus includes a handheld, portable housing which contains a data processor, an alarm, and a connecting device such as a jack that connects the apparatus to an external patient sensor. In response to the external sensor, the data processor activates the alarm to indicate that the patient has moved beyond the prescribed limit or that the senor has been improperly disconnected.

In one embodiment of the invention, the apparatus Includes a number of external sensors connected separately or together to the connecting device. These sensors may be, for example, door opening sensors, bed weight sensor, or tethers.

In another embodiment of the invention, the apparatus includes an internal sensor for sensing the position of the patient, such as whether the patient is attempting to arise from a prone position. To avoid sensor conflict, the data processor is programmed to disconnect the internal sensor when an external sensor is connected to the connecting device.

In another embodiment of the Invention, the apparatus Includes a data processor programmed to gather data concerning the quality of care administered to an attached patient. The data is obtained through various sensors and stored until transferred to a remote computer for evaluation.

The foregoing and other features and advantages of the invention will become more apparent from the following detailed description of a preferred embodiment which proceeds with reference to the accompanying drawings.

DETAILED DESCRIPTION OF A PREFERRED EMBODIMENT

Figure 1:
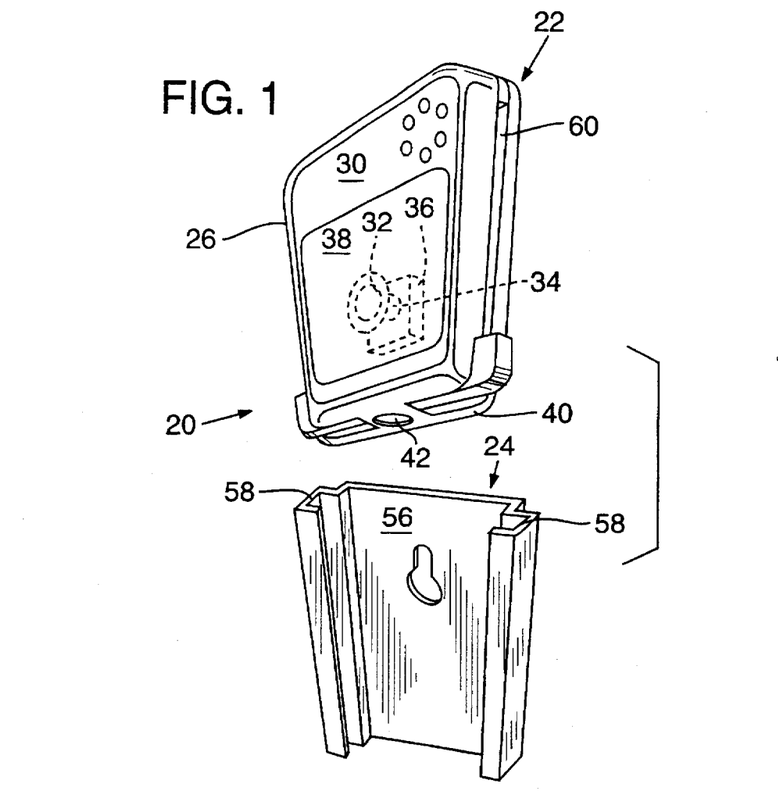
FIG. 1 is an isometric view of an apparatus according to the invention showing a master unit in conjunction with a mounting receptacle for mounting the master unit in a desired location.
Figure 2:
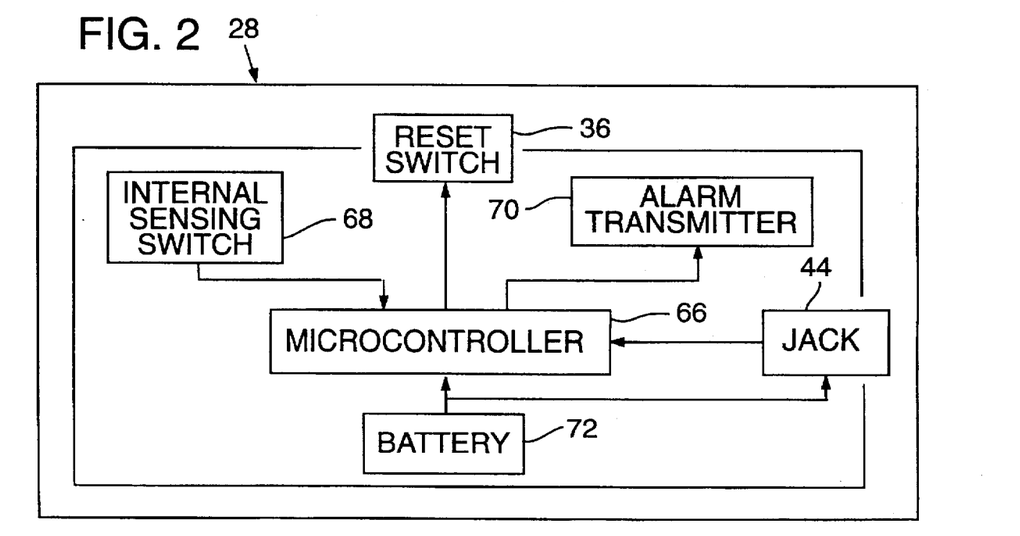
FIG. 2 is a block diagram of an electrical circuit within the master unit of FIG. 1.

FIGS. 1–3 show an apparatus 20 according to the invention comprising a master unit 22 and a mounting receptacle 24. Master unit 22 includes a portable housing 26 in which is contained an electrical circuit 28 on a printed circuit board. Housing 26 is a trapezoidal prism, preferably small enough in size to be hand held. Defined within a front side 30 of housing 26 is an aperture 32 through which a post 34 extends. The post connects to a pressure-activated reset switch 36 that is part of circuit 28. Covering the aperture and a portion of the front side 30 is a membrane 38 that prevents dust and moisture from entering the interior of the housing in the area of the switch. The membrane, however, is flexible enough to permit one to press through it to the post 34 to activate reset switch 36. Defined with a bottom side 40 of the housing is another aperture 42 through which an electrical connecting device such as a jack 44 may be reached. Electrical cables for external sensors may be inserted through aperture 42 to operatively connect the sensors to jack 44 and thereby to the electrical circuit 28.

Figure 3A:
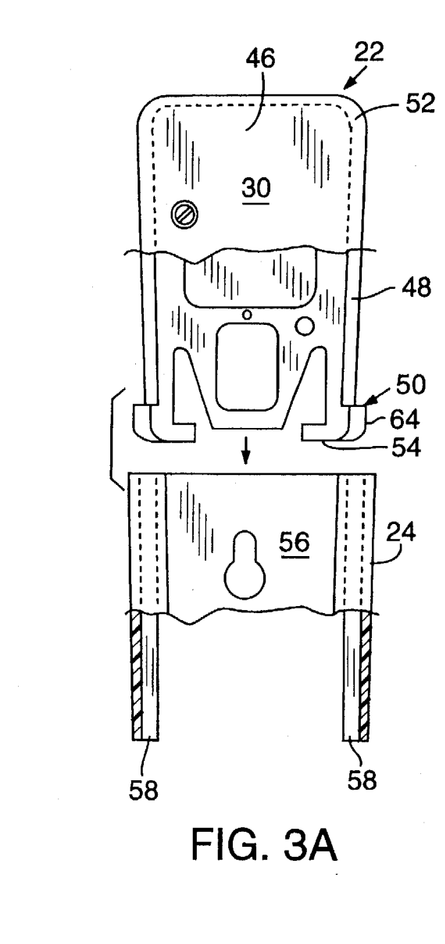
FIGS. 3A–D are a series of cut-away views showing how the master unit is inserted into the mounting receptacle, locked therein, and removed therefrom.

FIGS. 3A–D are a series of cut-away views showing how master unit 22 is inserted into mounting receptacle 24, locked therein, and removed therefrom. Referring to FIGS. 1 and 3A, master unit 22 includes a centerpiece 46 having a pair of resilient arms 48 that each taper inward and end in a catch 50. Each arm is notched between a top end 52 and a bottom end 54. The mounting receptacle includes a surface 56 supporting a pair of spaced-apart rails 58 that taper inward toward each other. The rails are substantially the length of the notched portion of the arms and are adapted to engage housing 26 in slots 60 (FIG. 1) defined by the arms 48 and the front side 30 and rear side 62 of the housing. Catch 50 includes a tab 64 adhered to the bottom arm end 54 for enabling one to press the arms 48 inward.

Figure 3B:
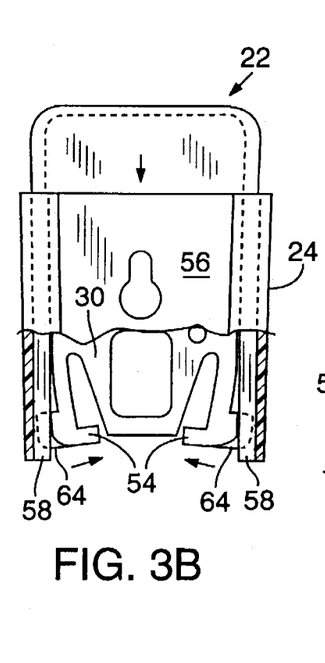

Referring to FIG. 3B, master unit 22 is shown slidingly engaged with rails 58 of mounting receptacle 24. Because of the tapering of the rails, arms 48 and especially their bottom ends 54 frictionally engage the rails as the master unit is inserted into the mounting receptacle. The tapering of the rails deflects catches 50 inward, but the catches are biased by the resiliency of the arms to press outward against the rails.

Figure 3C:
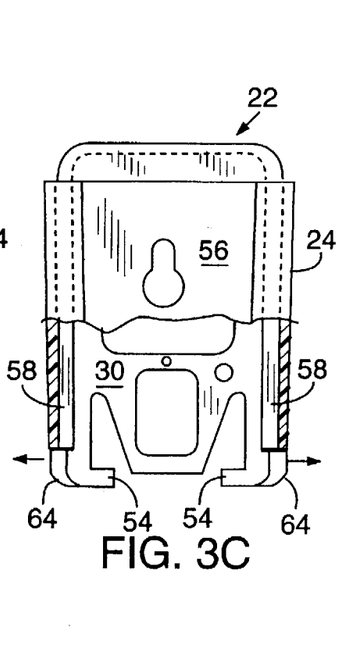

FIG. 3C shows master unit 22 securely locked into place within mounting receptacle 24. As the bottom ends 54 of the arms 48 slide past the bottom ends of rails 58, the bottom arm ends press outward to engage the bottom rail ends. Similarly, the top arm ends 52 engage the top rail ends to prevent the master unit from sliding further relative to receptacle 24.

Figure 3D:
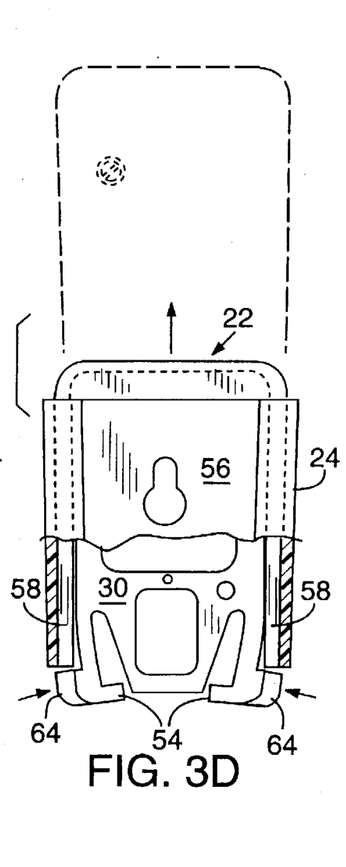

FIG. 3D shows how the master unit is removed from the mounting receptacle. Tabs 64 of catches 50 are simply pressed inward to disengage the bottom arm ends 54 from the bottom ends of rails 58 and the unit slid outward along the rails.

FIG. 2 is a block diagram of electrical circuit 28 within master unit 22. The circuit comprises a programmed data processor or controller such as a microcontroller 66 connected to jack 44, reset switch 34, an internal sensing switch 68, and alarm transmitter 70 and a battery 72. Microcontroller 66 is coupled to jack 44 to communicate with external sensors and other devices. Reset switch 34 is coupled to the microcontroller to reset master unit 22 in response to a press, in a manner to be described. Internal sensing switch 68 such as a level-sensitive mercury switch is also connected to the microcontroller to indicate when the switch is tilted beyond a predetermined angle. Alarm transmitter 70 generates an alarm in response to a microcontroller command. Transmitter 68 can take a variety of forms such as an audible or optical alarm, a wireless signal, a wired connection to a remote location or equivalent means. Battery 72 provides power to the electrical circuit as well as to devices connected to the circuit 28 which require power through jack 44.

Figure 4A:
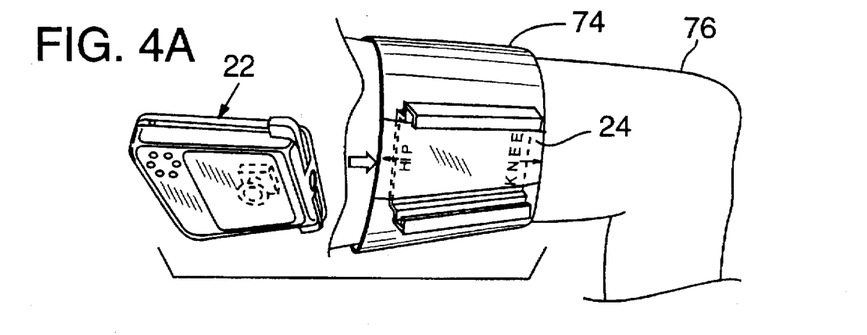
FIGS. 4A–C are a series of diagrams showing how the apparatus of FIG. 1 is used for monitoring the ambulatory position of a patient.
Figure 4B:
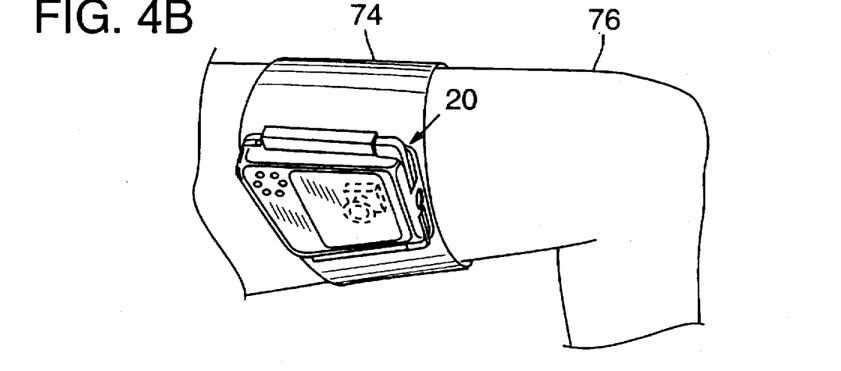
Figure 4C:
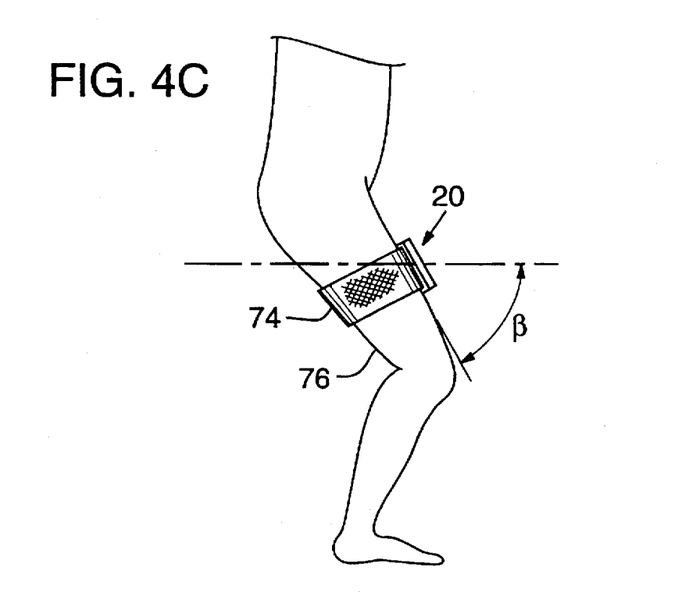

FIGS. 4A–C are a series of diagrams showing how apparatus 20 is used for monitoring the ambulatory position of a patient through an internal sensor such as a level-sensing switch. Mounting receptacle 24 is shown attached to a thigh clasp such as an elastic cloth band 74 which encircles a patient's thigh 76. In FIG. 4A, master unit 22 is shown being inserted into the mounting receptacle and in FIG. 4B the unit is locked in place. At the roughly horizontal angle of the unit shown therein, level sensing switch 68 is open and the master unit generates no alarm. If, as shown in FIG. 4C, the patient rises from this horizontal position past a predetermined angle β, mercury within the switch is drawn downward to make contact across a pair of electrodes. This closes the switch, sending a warning signal to microcontroller 66 that the patient has left a chair, bed or other position of confinement. The microcontroller in response generates an alarm for an attendant through alarm transmitter 70.

Figure 5:
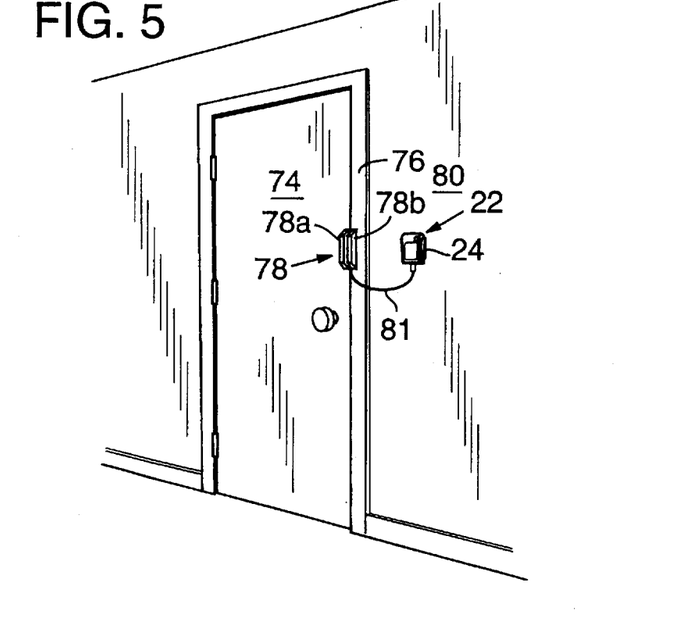
FIG. 5 is a diagram showing how the apparatus of FIG. 1 is used for monitoring the door of a room in which a patient is confined.

Apparatus 20, however, is not limited to sensing patient movement through internal switch 68. Microcontroller 66 can communicate with external sensors through jack 44, even providing power to them from battery 72. FIG. 5 is a diagram showing how the apparatus is used with an external sensor for monitoring the opening of a door 74 of a room in which a patient is confined. Mounted to the door and its adjacent door frame 76 is an external sensor in the form of a magnetic reed switch 78 of the type available from Tandy Corporation of Forth Worth, Tex. The reed switch includes a magnet 78a and a switch assembly 78b. The switch assembly includes a switch that is normally open when magnetically engaged to magnet 78a and closed when the magnet is moved a slight distance away. As shown in the figure, magnet 78a is attached near an edge of door 74 and switch assembly 78b is attached to a door frame 80 adjacent to the magnet. Master unit 22 is releasably secured nearby in mounting receptacle 24 attached to an adjacent wall 80. Switch 78 is then coupled to master unit 22 through a two-conductor cable 81 that passes through housing aperture 42 and connects to jack 44 to draw power from battery 72 and to pass signals to microcontroller 66. When door 74 is closed, magnet 78a and switch assembly 78b are close enough together for the magnet to keep the switch therein open. No current flows through cable 81 and no warning signal is communicated by switch 78 to the microcontroller. However, if door 74 is opened sufficiently to allow a person to pass through, magnet 78a is moved away from switch assembly 78b to cause the switch therein to close. This closing completes an electrical circuit through battery 72's switch assembly 78b and cable 81 to the microcontroller, causing a warning signal (logic high) to be sent to microcontroller 66. In response, the microcontroller generates an alarm through alarm transmitter 70, indicating that door 74 has been opened.

Figure 6:
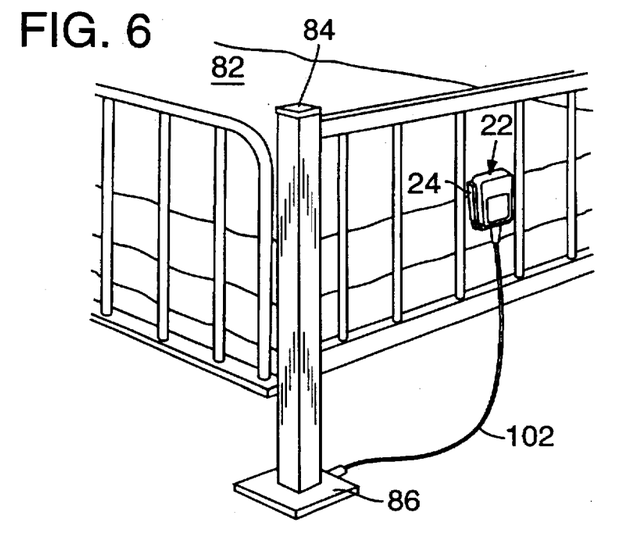
FIG. 6 is a diagram showing how the apparatus of FIG. 1 is used for monitoring a patient's presence in a bed.

FIG. 6 is a diagram showing how apparatus 20 is used for monitoring a patient's presence in a bed 82. Placed beneath a bed post 84 is a weight sensor in the form of a sensor pad 86 that senses a change in weight pressing upon it. The sensor generates a warning signal of a binary nature—no signal (logic low) if the weight is above a predetermined threshold and a warning signal (logic high) if the weight is below the threshold. Weight sensor 86 is coupled to master unit 22 through a three-wire cable 86 (power, ground and data) that connects to jack 44 and thereby to microcontroller 66. Master unit 22 is releasably secured in mounting receptacle 24 which is preferably attached to the frame 90 of bed 82 in a convenient location for inserting and removing the master unit. As with other external sensors, microcontroller 66 generates an alarm for an attendant through alarm transmitter 70 in response to a warning signal from sensor pad 86.

Figure 7:
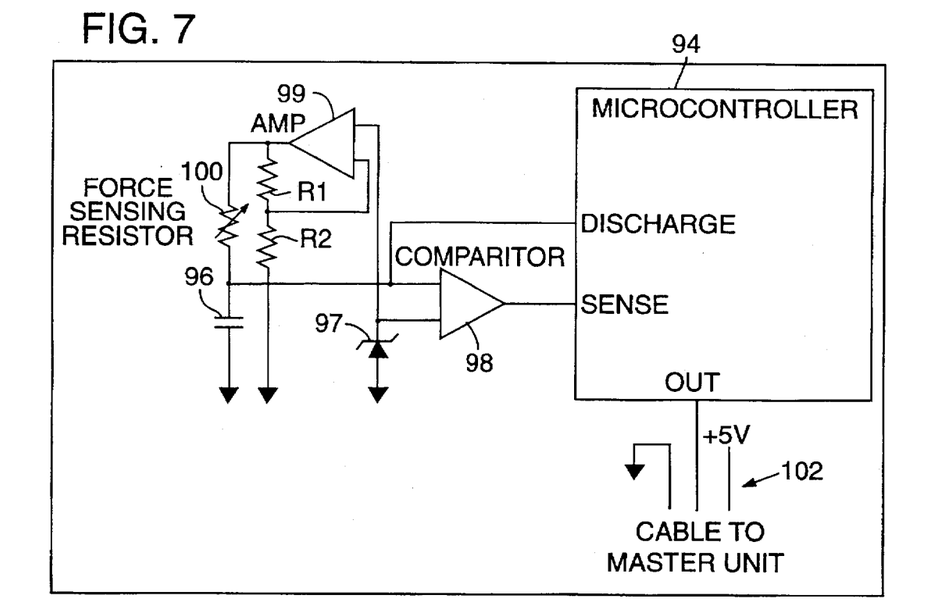
FIG. 7 is a circuit schematic diagram of a weight sensor pad shown in FIG. 6.

FIG. 7 is a diagram of a preferred form of weight sensor pad 86. A microcontroller 94 continuously measure the weight on the pad by repeatedly counting the time from the start of charging of a capacitor 96 until it exceeds a reference voltage 97, causing a comparator 98 to change state. The microcontroller then discharges the capacitor and repeats the process. Resistors R1 and R2 set the gain of an amplifier 99 such that the time measured is equal to the RC time constant of a force sensing resistor 100 and capacitor 96. Since the value of capacitor 96 is known, the microcontroller can calculate the force-related resistance of resistor 100 from the measured time. The calculated resistance relates to the weight (i.e., force) pressing downward upon resistor 100.

If microcontroller 94 determines that the resistance of resistor 100 has changed more than a predetermined amount within a given time, it sends a warning signal (logic high) to master unit 22 that the corresponding weight has changed. Microcontroller 66 responds to the warning signal by generating an alarm for an attendant through alarm transmitter 70. After notifying the master unit of the weight change, microcontroller uses the new resistance as a base resistance and continues to monitor for changes in weight. However, if no weight (i.e., negligible force/resistance) is sensed by microcontroller 94, it continuously sends a warning signal indicating that the sensor pad is not operating properly.

An electrical cable 102 is connected between sensor pad 86 and jack 44 to provide power and a communication link to the sensor pad.

Figure 8:
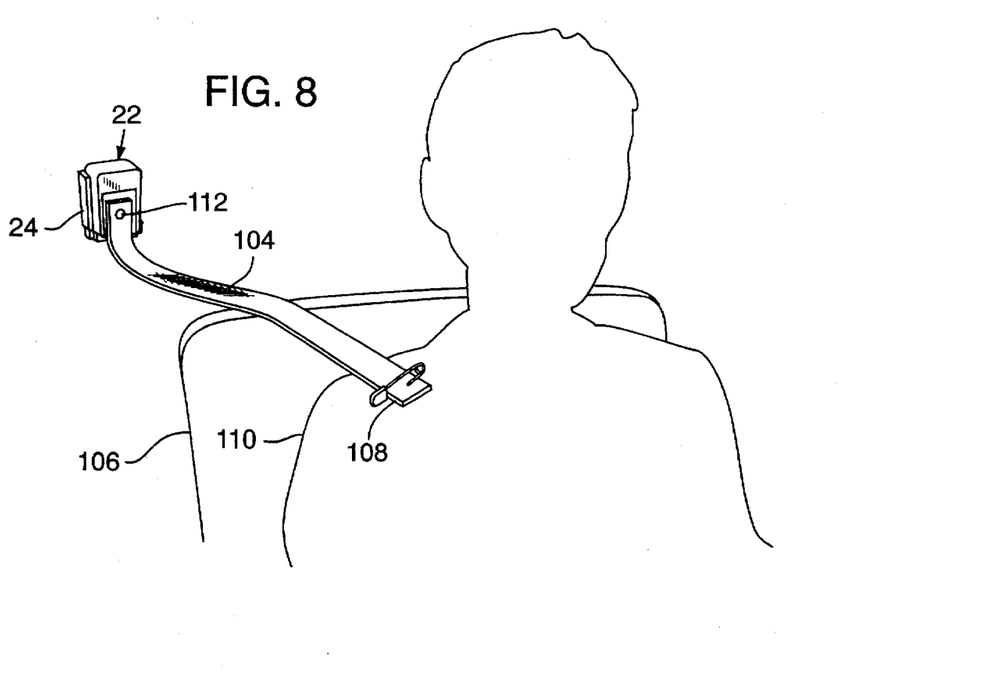
FIG. 8 is a diagram showing how the apparatus of FIG. 1 is used with a tether for monitoring a patient's presence in a confined area.

FIG. 8 shows how apparatus 20 uses a tether 104 for ensuring a patient remains in a small confined area, such as in a chair 106. One end 108 of the tether is attached to the patient's clothing 110. The other tether end includes a magnet 112 that is part of a switch such as a reed switch. The magnet is sized to fit within aperture 32 (FIG. 1) to contact a magnetic switch assembly within housing 26. With tether 104 in place, magnet 112 is engaged and the switch is closed. If the patient, however, pulls the tether and magnet away from master unit 22, the switch opens and sends a warning signal to microcontroller 66. The microcontroller responds by generating an alarm for an attendant through alarm transmitter 70.

Figure 9:
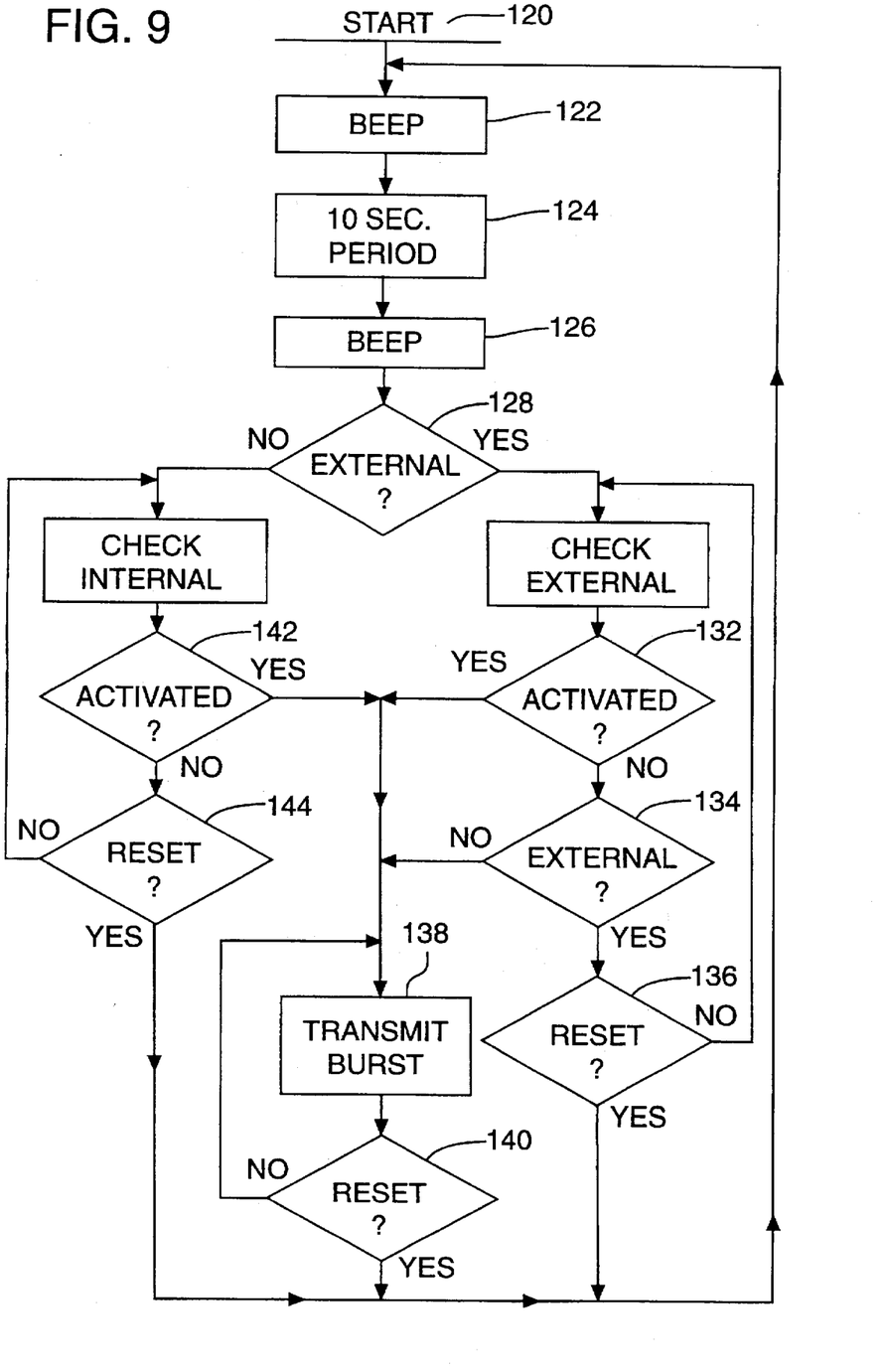
FIG. 9 is a flow chart of the operation of the master unit.

The operation of microcontroller 66 within master unit 22 is shown in the flow chart of FIG. 9. At the start (step 120), a user activates reset switch 36 by pressing post 34 twice within a two second period. Master unit 22 responds by emitting a one tone beep (step 122) from alarm transmitter 70 to acknowledge that the unit is in the reset state. Master unit then provides a ten second period (step 124) during which the user may change the alarm output level by pressing post 34 three times. The alarm level may be set from high to low or low to high. At the end of the ten second period, master unit emits another beep (step 126), one tone for selection of the high level output and two tones for selection of the low level output. If the user wants to change the alarm level at this point, he simply presses the reset switch again.

During the ten second period, the user may attach an external sensor such as weight sensor pad 86 or switch 78 to master unit 22 by inserting the plug of an associated electrical cable into jack 44. Following the output level selection beep, microcontroller 66 determines if a cable plug has been inserted into jack 44 (step 128). If so, the microcontroller does not check the status of the internal switch 68 (step 130) and enters a "check external" loop that checks the state of the external sensor connected to the master unit. As part of that loop the microcontroller awaits a warning signal from an external sensor via jack 44 (step 132). The microcontroller also detects whether the cable plug is impermissibly removed from jack 44, such as in an attempt to circumvent the external sensor (step 134) or whether the reset switch has been pressed (step 136). So long as none of these three events occurs, the microcontroller remains in the "check external" loop, repeating steps 132–136.

If and when the external sensor is activated or the cable plug removed from jack 44, microcontroller 66 responds by generating an alarm through alarm transmitter 70 (step 138). The alarm continues to be generated until reset switch 36 is pressed by the attendant (step 140). This returns the microcontroller to the start of its operation (step 120). Similarly, if the reset switch is pressed while the microcontroller is in its "check external" loop (step 136), the microcontroller returns to step 120.

If no cable plug is detected in jack 44 (step 128), then the microcontroller enters a "check internal" loop that checks the state of internal switch 68. As part of that loop the microcontroller awaits a warning signal from the switch (step 142). The microcontroller also detects whether the reset switch has been pressed (step 144). So long as neither of these events occurs, the microcontroller remains in this loop, repeating steps 142–144.

If and when internal switch 68 is activated, microcontroller 66 responds by generating an alarm through alarm transmitter 70 (step 138). The alarm continues to be generated until reset switch 36 is pressed by the attendant (step 140). This returns the microcontroller to the start of its operation (step 120). Similarly, if the reset switch is pressed while the microcontroller is in its "check internal" loop (step 144), the microcontroller returns to step 120.

Microcontroller 66 is also programmed to store in its memory quality assurance data for evaluating the nature of care provided to the patient. The data may be recovered in a number of ways, such as by removing master unit 22 from receptacle 24 and connecting microcontroller 66 via a cable and jack 44 to a remote computer that can access the data. The collected may data include the date of the last alarm reset; the number of alarms that have occurred since the data was last recovered; the total time of alarms; and the longest time from alarm to reset. From this data, the computer can calculate the average time required to respond to the patient's alarms and other important statistics. After downloading the data into the remote computer, a user may clear the data from microcontroller 66 and provide it with the current date.

Having illustrated and described the principles of the invention in a preferred embodiment, it should be apparent to those skilled in the art that the preferred embodiment can be modified in arrangement and detail without departing from such principles. For example, many of the software aspects of the embodiment may be implemented in hardware and vice versa. The described operation of the microcontroller is but one of many equivalent ways of carrying out its operation. The arrangement of switches may be varied in ways known to those of skill in the art. And the type of switches and sensors may vary. For example, other external sensors may include a sensor for detecting moisture to indicate incontinence or a sensor for detecting oxygen to indicate that oxygen is available in a patient's breathing apparatus.

In view of the many possible embodiments to which the principles of the invention may be applied, it should be recognized that the illustrated embodiment is only a preferred example of the invention and should not be taken as a limitation on its scope. Rather, the invention is limited only by the scope of the following claims. We therefore claim as the invention all that comes within the scope of these claims.

We claim:

1. Apparatus for monitoring movement of a patient in a plurality of ways, comprising:

a connecting device for alternatively connecting to a plurality of different external sensors connectable to the device;

a data processor coupled to the connecting device and responsive to an external sensor connected to the connecting device for determining whether the patient has moved beyond a limit and for determining whether the external sensor has been improperly disconnected from the connecting device;

an alarm responsive to the data processor for indicating that the patient has moved beyond the limit or that the external sensor has been improperly disconnected; and a handheld, portable housing for containing the device, data processor and alarm, wherein the data processor is adapted to respond to the plurality of different external sensors.

2. The apparatus of claim 1 including an external sensor for sensing the opening of a door, the sensor generating a binary signal for indicating whether the door is open or closed.

3. The apparatus of claim 1 including an external sensor for sensing a patient's weight on a piece of furniture, the sensor generating a binary signal for indicating whether the patient is present on or absent from the furniture.

4. The apparatus of claim 1 including:

a switch actuable in response to its disconnection from a tether, the switch coupled to the data processor; and the tether having one end for operative connection to the switch and another end for operative connection to a patient, the data processor actuating the alarm in response to actuation of the switch.

5. The apparatus of claim 1 including a power source for providing power to the external sensor through the connecting device.

6. The apparatus of claim 1 including a reset switch actuable in response to a command for allowing proper disconnection of an external sensor from the connecting device.

7. Apparatus for monitoring movement of a patient, comprising:

a connecting device for operatively connecting to an external sensor;

a data processor coupled to the connecting device and responsive to the external sensor for determining whether the patient has moved beyond a limit and for determining whether the external sensor has been improperly disconnected from the connecting device;

an alarm responsive to the data processor for indicating that the patient has moved beyond the limit or that the external sensor has been improperly disconnected;

a handheld, portable housing for containing the connecting device, data processor and alarm; and a reset switch actuable to produce a command in the data processor for allowing proper connection of an external sensor to the connecting device.

8. Apparatus for monitoring movement of a patient, comprising:

a connecting device for removably connecting to an external movement sensor;

a data processor coupled to the connecting device and responsive to the external sensor for determining whether the patient has moved beyond a limit;

memory for storing data collected by the data processor;

an alarm responsive to the data processor for indicating that the patient has moved beyond the limit; and a portable housing for containing the connecting device, data processor and alarm, the data processor programmed to store in the memory a set of quality assurance data for evaluating the nature of care provided to the patient, the stored data being recoverable by a remote computer operatively connected to the memory, wherein the set of quality assurance data includes the date of the last alarm; the number of alarms that have occurred since the data was last recovered; the total time of alarms; and the longest time from alarm to reset.

9. Apparatus for monitoring movement of a patient, comprising:

a connecting device for operatively connecting to an external sensor;

a data processor coupled to the connecting device and responsive to the external sensor for determining whether the patient has moved beyond a limit and for determining whether the external sensor has been improperly disconnected from the connecting device;

an alarm responsive to the data processor for indicating that the patient has moved beyond the limit or that the external sensor has been improperly disconnected;

a handheld, portable housing for containing the connecting device, data processor and alarm; and an internal sensor within the housing for sensing the position of the patient, the sensor actuable In response to a preselected amount of downwardly directed inclination.

10. The apparatus of claim 9 including means for attaching the housing to a leg of a patient.

11. The apparatus of claim 9 wherein the data processor is adapted to disconnect the internal sensor in response to the connection of an external sensor to the connecting device.

* * * * *